US008603569B2

(12) United States Patent
Bayer et al.

(10) Patent No.: US 8,603,569 B2
(45) Date of Patent: Dec. 10, 2013

(54) IMPLANT AND METHOD FOR PRODUCING A DEGRADATION-INHIBITING LAYER ON THE SURFACE OF AN IMPLANT BODY

(75) Inventors: Ullrich Bayer, Admannshagen-Bargeshagen (DE); Baerbel Becher, Rostock (DE); Bernd Block, Rostock (DE)

(73) Assignee: Biotronik VI Patent AG, Baar (CH)

( * ) Notice: Subject to any disclaimer, the term of this patent is extended or adjusted under 35 U.S.C. 154(b) by 416 days.

(21) Appl. No.: 12/566,571

(22) Filed: Sep. 24, 2009

(65) Prior Publication Data

US 2010/0087916 A1 Apr. 8, 2010

(30) Foreign Application Priority Data

Oct. 6, 2008 (DE) .................. 10 2008 042 603

(51) Int. Cl.
*A61L 33/00* (2006.01)
*B05D 3/00* (2006.01)
*B05D 1/18* (2006.01)

(52) U.S. Cl.
USPC ........ 427/2.24; 427/2.1; 427/2.25; 427/430.1

(58) Field of Classification Search
USPC .......... 427/2.1, 2.24, 2.25, 430.1, 435, 443.2; 623/1.15, 1.42, 1.44
See application file for complete search history.

(56) References Cited

U.S. PATENT DOCUMENTS

| 4,073,999 | A | * | 2/1978 | Bryan et al. ............... 428/312.8 |
| 5,788,558 | A | * | 8/1998 | Klein .............................. 451/36 |
| 6,997,949 | B2 | * | 2/2006 | Tuch ............................ 623/1.42 |
| 2004/0243225 | A1 | * | 12/2004 | Ragheb et al. ............... 623/1.42 |
| 2004/0254608 | A1 | | 12/2004 | Huitema et al. |
| 2005/0019366 | A1 | * | 1/2005 | Zeldis ........................... 424/423 |
| 2006/0121080 | A1 | * | 6/2006 | Lye et al. ...................... 424/423 |
| 2006/0121113 | A1 | * | 6/2006 | Bartholomaeus ............ 424/468 |
| 2006/0239932 | A1 | * | 10/2006 | Monteith et al. ................ 424/46 |
| 2007/0099819 | A1 | | 5/2007 | Glidden |
| 2007/0207186 | A1 | | 9/2007 | Scanlon et al. |
| 2007/0293937 | A1 | * | 12/2007 | Biggs et al. .................. 623/1.13 |
| 2008/0243242 | A1 | * | 10/2008 | Kappelt et al. ............... 623/1.46 |
| 2011/0076319 | A1 | | 3/2011 | Orlowski et al. |

FOREIGN PATENT DOCUMENTS

| DE | 10 2007 004 589 A1 | 7/2008 |
| EP | 1 913 962 A1 | 4/2008 |
| WO | 2008045184 A1 | 4/2008 |

OTHER PUBLICATIONS

German search report for priority application DE 10 2008 042 603.2.
European Search Report for EP 09169483.6.
Pentel KK, XP002699641, Abstract of JP H07 268380, Oct. 17, 1995.
Toyo Rubber Chem Ind Co, XP002699642, Abstract of JP S53 5264A, Jan. 18, 1978.
Daihatsu Motor Co Ltd, XP002699643, Abstract of JP H09 241861 A, Sep. 16, 1997.

* cited by examiner

*Primary Examiner* — Michael Wieczorek
(74) *Attorney, Agent, or Firm* — Biotech Beach Law Group PC

(57) ABSTRACT

A method for manufacturing a degradation-inhibiting first layer on the surface of an implant body, in particular an intraluminal endoprosthesis, whereby the body has at least one metallic material, which is at least largely biodegradable, comprising the following steps: preparing the body of the implant, and applying the first layer to at least a portion of the body surface, whereby the first layer contains magnesium stearate. An implant obtainable by such a method.

20 Claims, No Drawings

IMPLANT AND METHOD FOR PRODUCING A DEGRADATION-INHIBITING LAYER ON THE SURFACE OF AN IMPLANT BODY

CROSS REFERENCE TO RELATED APPLICATIONS

This invention claims benefit of priority to Germany patent application serial number DE 10 2008 042 603.2, filed on Oct. 6, 2008; the contents of which are herein incorporated by reference in their entirety.

TECHNICAL FIELD

The invention relates to a method for producing a degradation-inhibiting first layer on the surface of an implant body, in particular an intraluminal endoprosthesis, where the body has at least one metallic material that is at least largely biodegradable, and an implant obtainable or obtained by such a method.

BACKGROUND OF THE INVENTION

Medical endoprostheses or implants for a wide variety of applications are known in a great variety from the prior art. Endoprostheses in the sense of the present invention include, for example, endovascular prostheses, e.g., stents, fastening elements for bones, e.g., screws, plates or nails, surgical suture materials, intestinal clamps, vascular clips, prostheses for use in the area of hard and soft tissue as well as anchoring elements for electrodes, in particular pacemakers or defibrillators.

Stents are used especially commonly today as implants for treatment of stenoses (vascular occlusions). They have a basic mesh which is tubular or hollow cylindrical and is open at both longitudinal ends. The tubular basic mesh of such an endoprosthesis is inserted into the vessel to be treated and serves to support the vessel. Stents have become established for treatment of vascular diseases in particular. Through the use of stents, constricted areas in the vessels can be dilated, resulting in a larger lumen. Although an optimum vascular cross section can be achieved through the use of stents or other implants, and this is one of the primary requirements for successful treatment, the permanent presence of such a foreign body initiates a cascade of microbiological processes which can lead to a gradual overgrowth of the stent and, in the worst case, to a vascular occlusion. One starting point toward solving this problem is to manufacture the stent and/or other implants from a biodegradable material.

The term "biodegradation" is understood to refer to hydrolytic, enzymatic and other metabolic degradation processes in a viable organism, caused primarily by the body fluids coming in to contact with the biodegradable material and leading to gradual dissolution of the structures of the implant containing the biodegradable material. Through this process, the implant loses its mechanical integrity at a certain point in time. The term "biocorrosion" is often used as synonymous with the term biodegradation. The term "bioresorption" includes the subsequent absorption of the degradation products by the living organism.

Materials suitable for the basic mesh of biodegradable implants may contain polymers or metals, for example. The basic mesh may comprise several of these materials. The feature these materials have in common is their biodegradability. Examples of suitable polymeric compounds include polymers from the group of cellulose, collagen, albumin, casein, polysaccharides (PSAC), polylactide (PLA), poly-L-lactide (PLLA), polyglycol (PGA), poly-D,L-lactide-co-glycolide (PDLLA-PGA), polyhydroxybutyric acid (PHB), polyhydroxyvaleric acid (PHV), polyalkyl carbonates, polyorthoesters, polyethylene terephthalate (PET), polymalonic acid (PML), polyanhydrides, polyphosphazenes, polyamino acids and their copolymers as well as hyaluronic acid. Depending on the desired properties, the polymers may be in pure form, in derivatized form, in the form of blends or copolymers. Metallic biodegradable materials are based primarily on alloys of magnesium and iron. The present invention preferably relates to implants whose biodegradable material contains at least partially a metal, preferably magnesium or a magnesium alloy.

Stents having coatings with different functions are already known. Such coatings serve to release medicines, to arrange an X-ray marker or to protect the underlying structures, for example.

In the implementation of biodegradable implants, the degradability should be controlled in accordance with the desired treatment and/or use of the respective implant (coronary, intracranial, renal, etc.). For many therapeutic applications, for example, an important target corridor is for the implant to lose its integrity over a period of four weeks to six months, for example. Integrity here is understood to be mechanical integrity, i.e., the property whereby the implant suffers hardly any mechanical losses at all in comparison with the undegraded implant. This means that the implant still has such great mechanical stability that the collapse pressure, for example, drops only slightly, i.e., to at most 80% of the nominal value. The implant may thus still fulfill its main function, i.e., keeping the blood vessel open, if it still has integrity. Alternatively, the integrity may be defined by the fact that the implant has such great mechanical stability that, in its stressed state in a blood vessel, it is hardly subject to any geometric changes, e.g., it does not undergo any mentionable collapse, i.e., it still has at least 80% of the dilatation diameter under load or, in the case of a stent, hardly any of the struts are broken.

Biodegradable magnesium implants, in particular magnesium stents have proven to be especially promising for the aforementioned target corridor of degradation, but, first of all, they lose their mechanical integrity, i.e., the supporting effect, too soon and on the other hand have a greatly fluctuating loss of integrity in vitro and in vivo. This means that in the case of the magnesium stents, the collapse pressure drops too rapidly over time and/or the reduction in the collapse pressure has too much variability and therefore cannot be determined.

Various mechanisms for controlling the degradation of magnesium implants have already been described in the prior art. These are based, for example, on organic and inorganic protective layers or combinations thereof which counteract the human corrosion medium and present resistance to the corrosion processes taking place there. Approaches known in the past have been characterized in that they achieve barrier layer effects which are based on a spatial separation that is as complete as possible between the corrosion medium and the metallic material, in particular the metallic magnesium. The degradation protection is thus ensured by protective layers having various compositions and by defined geometric distances (diffusion barriers) between the corrosion medium and the magnesium base material. Other approaches are based on the alloy components of the biodegradable material of the implant body which influence the corrosion process by displacing the location in the electrochemical voltage series. Other approaches in the field of controlled degradation induce predetermined breaking effects by applying physical changes (e.g., local changes in cross section) and/or chemical changes in the stent surface (e.g., multiple layers having different chemical compositions). However, with the approaches mentioned so far, it is usually impossible to have the dissolution that occurs due to the degradation process and to have the resulting breakage of webs occur within the required time frame. The result is that either the onset of degradation is too early or too late and/or there is too much variability in the degradation of the implant.

Another problem that occurs in conjunction with passivation coatings is based on the fact that stents or other implants usually assume two states, namely a compressed state with a small diameter and an expanded state with a larger diameter. In the compressed state, the implant can be inserted into the vessel to be supported by means of a catheter and can be positioned at the site to be treated. At the site of treatment, the implant is then dilated by means of a balloon catheter and/or (when using a shape memory alloy as the implant material) converted to the expanded state, e.g., by heating to a temperature above the transition temperature. On the basis of this change in diameter, the body of the implant here is exposed to a mechanical stress. Additional mechanical stresses on the implant may occur during production or in the movement of the implant in or with the vessel into which the implant is inserted. With the known coatings, this yields the disadvantage that the coating cracks during deformation of the implant (e.g., forming microcracks) or is even partially removed. This may cause an unspecified local degradation. Furthermore, the onset and rate of degradation depend on the size and distribution of the microcracks, which are formed due to deformation and, as defects, are difficult to control. This leads to a great scattering in the degradation times.

The document DE 10 2006 060 501 discloses a method for manufacturing a corrosion-inhibiting coating on an implant made of a biocorrodible magnesium alloy and an implant obtainable by this method in which, after the implant has been prepared, the implant surface is treated with an aqueous or alcoholic reaction solution containing one or more ions selected from the group comprising $K^+$, $Na^+$, $NH_4^-$, $Ca^{2+}$, $Mg^{2+}$, $Zn^{2+}$, $Ti^{4+}$, $Zr^{4+}$, $Ce^{3+}$, $Ce^{4+}$, $PO_3^{3-}$, $PO_4^{3-}$, $HPO_4^{2-}$, $H_2PO_4^-$, $OH^-$, $BO_3^{3-}$, $B_4O_7^{3-}$, $SiO_3^{2-}$, $MnO_4^{2-}$, $MnO_4^-$, $VO_3^-$, $WO_4^{2-}$, $MoO_4^{2-}$, $TiO_3^{2-}$, $Se^{2-}$, $ZrO_3^{2-}$ and $NbO_4^-$, where the concentration of ion(s) is in the range of $10^{-2}$ mol/L to 2 mol/L. The treatment of the implant surface with the aforementioned reaction solution necessitates anodic oxidation of the implant. It is performed either with or without an external current source (externally currentless). However, the examples of methods and electrolyte compositions described in this document do not meet expectations with regard to degradation behavior and dilatation ability without destruction of the layer when used for a magnesium stent.

BRIEF SUMMARY OF THE INVENTION

The object of the present invention is thus to provide a method for manufacturing a degradation-inhibiting first layer on a body of an implant, which will permit degradation of the implant in the desired target corridor. The degradation should take place at a controllable point in time and should additionally allow dilatation and/or deformation of the implant without any mentionable influence on the degradation behavior. Accordingly, the object of the invention also includes creating such an implant and the implant itself.

The object defined above is achieved by a method comprising the following steps: a) preparing the body of the implant, and b) applying the first layer to at least a portion of the body surface, where the first layer contains magnesium stearate.

DETAILED DESCRIPTION OF THE INVENTION

In one aspect of the present invention, a method is provided, which comprises the following steps: a) preparing the body of the implant, and b) applying the first layer to at least a portion of the body surface, where the first layer contains magnesium stearate. In another aspect of the present invention the implant is provided.

The body of the implant comprises at least a portion of the implant, preferably most of the implant which produces the mechanical integrity of the implant.

By means of the present method, it is possible to produce an implant which is characterized in that the surface of the body is free of defects due to subsequent sealing with the first layer. Local defects and/or pores present in the body of the implant are effectively protected from contact with body fluids that have a corrosive effect. The hydrophobic surface property and a low of water of crystallization content of magnesium stearate, which is also produced by a subsequent drying step performed after applying the first layer, result in an extremely low diffusion of water to the base material of the implant body. Both the local contaminants at the surface of the implant due to the production process and the deposits at the surface due to the alloy composition of the implant body are embedded in the magnesium stearate, where they are inert and therefore can no longer react with the ambient conditions. Likewise, the release of particles with a low binding tendency from the surface of the implant body in dilatation is also prevented. These particles remain in the tough, highly flexible magnesium stearate layer. This results in an increased hemocompatibility and/or biocompatibility.

Due to the first layer produced by means of the inventive method, the storage and shipping conditions of the implants produced by the inventive method are simplified because the stability of such an implant with respect to degradation is greater than that of uncoated implants.

Because of the coating of the implant body with the first layer, this advantageously achieves the result that the coefficient of friction of the implant is reduced. It follows from this that in displacement of a stent as an implant in a catheter, for example, lower forces must be expended. Therefore, in the case of a stent, more accurate stent fixation is achieved. Furthermore, the crimping and the subsequent release of the implant at the site of treatment are simplified.

In a preferred exemplary embodiment of the inventive method, the first layer is applied by immersion in a solution, where the solution contains magnesium stearate and a solvent, preferably acetone or isopropanol, and preferably has a temperature between approx. 10° C. and 40° C. Alternatively, the magnesium stearate layer may also be applied in such a way that said solution containing magnesium stearate is sprayed onto the body of the implant (spray coating). Then this part is suspended on a thin wire in a chamber and is sprayed on all sides by means of a rotating plate (batch mount).

In a preferred exemplary embodiment, the efficacy of the immersion process can be increased by applying a pressure, which is less than ambient pressure, preferably less than approx. 90% of ambient pressure, i.e., atmospheric pressure at the site where the immersion process is performed. The resulting degassing effect leads to rapid filling of the filigree surface structure of the implant with magnesium stearate.

It is also advantageous if the implant body has a rough surface before being coated with magnesium stearate. This improves adhesion of the first layer to the implant body.

After a dwell time of a few minutes in the solution, preferably at least approx. two minutes, the coated body is removed from the immersion bath and dried in a drying oven at a temperature higher than room temperature, preferably higher than approx. 30° C. It is especially preferable here if the drying temperature is as low as possible, i.e., between approx. 40° C. and approx. 70° C. because this leads to a slow release/evaporation of the at least one solvent, which creates a pore-free first layer containing magnesium stearate.

The efficacy of the magnesium stearate coating can be demonstrated, for example, by displacing the implant in a tubular test device, e.g., a stent in a catheter. Because of the magnesium stearate coating, when the implant is displaced in the test device, lower forces must be applied. In addition, the sealing effect achieved by the magnesium stearate can be proven by in vitro storage in artificial plasma. Sealing by the magnesium stearate coating leads to a lower reduction in the metallic cross section during storage in comparison with an implant without a coating.

In another exemplary embodiment of the present invention, before applying the first layer and after preparing the body of the implant, at least a portion of the body surface is subjected to a plasma chemical treatment to create an intermediate layer. The plasma chemical treatment comprises treatment in an aqueous electrolyte system (aqueous solution) in which plasma chemical effects occur directly at the surface of the implant body. The plasma remains stable for a few microseconds at the surface of the body, producing reaction products that lead to the development of the intermediate layer on the body surface. The intermediate layer is preferably arranged on a corresponding part or the entire body surface of the implant, such that the intermediate layer between the body surface and the first layer contains the magnesium stearate.

Due to the plasma chemical treatment, phosphates, hydroxides and oxides of the metallic material, in particular magnesium, are formed on the surface of the implant body. This composition of the layer forms a temporary corrosion protection in contact with body fluid, causing delayed degradation of the metallic material. The particles released in the wake of the delayed degradation of the implant are partially incorporated by endogenous cells and/or are further degraded. The degradation-inhibiting layer produced by the inventive method has pores due to the process, initially forming naturally corrosive weak spots through which contact of the electrolyte with the metallic base material is facilitated. However, the analytical surface tests performed before and after the degradation test have shown that the hydroxide production associated with the plasma chemical treatment leads to a locally limited sealing of the bases of the pores as described below.

The sealing of the bases of the pores may be demonstrated, for example, on the basis of a multistep course of the pH of an electrolyte in a corrosion test (e.g., artificial plasma). In the first seven days, the pH rises from 7.4 to 8.5 to 8.7, as expected. When a media change is performed after seven days, the pH surprisingly rises from 7.4 to only 8.0. This method shows a lower chemical activity of the metallic base material (in particular the magnesium) with the corrosive medium. This effect is associated with stopping the reduction in cross section of the material of the implant body which is detectable after only seven days in the metallographic polished section. This effect can be explained, for example, by the fact that the hydroxides of the metallic material fill up the pores in the intermediate layer and thus prevent contact between the electrolyte and the metallic base material. Due to this self-healing effect, the lifetime of the implants under the conditions prevailing in the body is significantly increased. Furthermore, the rate of degradation can be controlled by varying the layer thickness. This leads to the possibility of adjusting the degradation time of the implant to the specific implantation site (coronary, intracranial, renal, etc.).

Another advantage of the plasma chemical process is that the surface contamination of the base material that cannot be removed by the preceding processes of treatment of the implant surface are absorbed by the degradation-inhibiting intermediate layer and therefore are no longer affected by the additional influence of the degradation process in a negative sense. Furthermore, excretions of the implant body, some of which are protruding out of the surface (containing, for example, undissolved alloy components, e.g. yttrium and its compounds) are covered. This yields a further increase in hemocompatibility and/or biocompatibility.

Furthermore, the structure of the intermediate layer, which is porous due to the process, has a high plastic deformation capacity. For example, the microcracks that occur in dilatation of a stent are stopped by an accumulation of energy and/or dissipation of energy in the pores adjacent to the microcracks. There is therefore no delamination of the intermediate layer.

The aqueous solution preferably contains one or more ions selected from the group of phosphates, carbonates, hydroxides and silicates. In an especially preferred exemplary embodiment, the aqueous solution contains $Sr^{2-}$ ions, which are preferably present in a concentration of approx. 0.05 mol/L to approx. 2.0 mol/L $Sr^{2-}$ ions in the aqueous solution. In this way, strontium compounds are incorporated into the intermediate layer, i.e., the surface layer of the implant. This is advantageous because strontium carbonate in particular has hardly any solubility in water and thus forms a component in the surface layer which inhibits degradation in particular. Furthermore, the strontium carbonate present in the coating in cranial applications in particular may manifest a drug-like effect against cerebral sclerosis.

The implant treated by plasma chemical coating is then rinsed in a solvent, preferably distilled $H_2O$, and next dried, preferably at a temperature of at least approx. 80° C., especially preferably at least approx. 100° C., where the drying is preferably performed in a circulating air oven.

To keep the pH of the electrolyte (aqueous solution) constant, it is preferable for the aqueous solution to contain a buffer, preferably potassium dihydrogen phosphate and/or sodium dihydrogen phosphate.

In another preferred exemplary embodiment, the implant body is treated electrochemically prior to the plasma chemical treatment, preferably being electrochemically polished. This removes implants on the surface of the implant body, so that the plasma chemical treatment takes place on a defined surface.

The plasma chemical treatment of the implant body is preferably performed by applying a pulsed positive voltage to the body, the amplitude of this voltage exceeding at least approx. 90 volt over most of the period of time, especially preferably exceeding at least approx. 100 volt and preferably rising in the course of the treatment. Due to these high pulsed voltages with a pulse length of preferably max. approx. 20 microseconds, especially preferably approx. 5 microseconds, plasmas which lead to reaction of the metallic material of the implant body with the electrolyte are generated at the surface of the implant body for microseconds. Between the voltage pulses there is a resting phase of preferably approx. 100 microseconds.

The plasma chemical process is preferably performed at a current density of at least approx. 8 mA/cm$^2$, preferably at least approx. 10 mA/cm$^2$.

In another preferred exemplary embodiment, a second layer, preferably a layer consisting at least predominantly of parylene, can be applied to the first layer. Preferred layer thicknesses of the parylene layer are between approx. 0.1 and 10 μm. Due to such a layer combination, the degradation time of the implant can be increased again significantly. Parylene here is the term for completely linear, partially crystalline, uncrosslinked aromatic polymers. The various polymers have different properties and can be divided into four basic types, namely parylene C, parylene D, parylene N and parylene F. When using the parylene N variant, a very uniform degradation pattern is the result. This means that the surface corrosion comes closest to the a desired degradation target corridor when using the combination used in a preferred exemplary embodiment, namely a combination of a magnesium stearate layer, a plasma chemical layer and a second layer with parylene N.

The above object is also achieved by an implant obtainable by the inventive method described above. The object is also achieved by an implant having a first layer containing magnesium stearate over at least a portion of its surface.

The inventive implants have the advantages indicated above in conjunction with the inventive manufacturing method.

In a preferred exemplary embodiment of the present invention, the thickness of the first layer amounts to approx. 0.5 μm to approx. 10 μm preferably approx. 1.0 μm to approx. 5.0 μm. The concentration of the magnesium stearate in the first layer is between approx. 80 wt % and 100 wt %. It is advantageous in particular with regard to the biocompatibility of the first layer if the layer is dried and thus degassed until the solvent is completely evaporated.

The first intermediate layer created by means of the plasma chemical treatment preferably has a thickness of approx. 1 to 20 μm, preferably approx. 1 to 8 μm. A layer with a thickness of approx. 2 to 5 μm is to be favored due to the higher plastification capacity.

It has already been described above that the intermediate layer contains pores, with the hydroxide of the metallic material(s) of the implant body preferably being formed at the base of the pores. Due to the hydroxide arranged at the base of the pores, a locally limited sealing of the base of the pores is achieved.

The intermediate layer preferably contains at least one compound selected from the group of phosphates, hydroxides and oxides of the biodegradable material(s), strontium carbonate, strontium phosphate.

The inventive method is explained in greater detail below on the basis of an example. All the features described here form the subject of the invention independently of how they are combined in the claims or their reference back to previous claims.

First, an implant in the form of a stent with a body consisting of a magnesium alloy, preferably WE43 (93 wt % magnesium, 4 wt % yttrium (W) and 3 wt % rare earth metals (E) in addition to yttrium) is prepared.

Next an aqueous solution (electrolyte) is prepared. To do so, 500 mL distilled H$_2$O is first added to a glass beaker. Then the components are added to the aqueous solution in the order given below. It should be noted here that the next component must not be added until after the previous components have dissolved completely. The electrolyte is to be stirred continuously during this addition, which can be implemented by using a magnetic stirrer (500 min$^{-1}$), for example. The components should be added extremely slowly to prevent an excessive evolution of heat. Alternatively, the electrolyte synthesis may also be performed in a double-walled coolable container. The following components may be added:
1. 100 mL/L ethylenediamine solution (99%),
   100 g/L potassium dihydrogen phosphate.
   90 g/L strontium hydroxide octahydrate and
   40 mL/L aqueous ammonium hydroxide solution (25%)
or
2. 50 mL/L ethylenediamine solution (99%),
   50 g/L potassium dihydrogen phosphate,
   90 g/L strontium nitrate and
   20 mL/L aqueous ammonium hydroxide solution (25 wt %) or 25 g/L sodium hydroxide The following compositions may be selected alternatively for a plasma chemical coating in an aqueous solution without Sr$^{2-}$ ions:

|  | Ethylenediamine solution (99%) | Potassium dihydrogen phosphate | Aqueous ammonium hydroxide solution (25%) | Sodium hydroxide |
|---|---|---|---|---|
| 3. | 30 mL/L | 10 g/L | 10 mL/L | 0 |
| 4. | 30 mL/L | 10 g/L | 0 | 10 g/L |

After completion of one of the batches labeled as 1, 2, 3 or 4, the plasma chemical coating process takes place.

Before the plasma chemical coating process, a multistage degreasing may be performed in solutions containing a surfactant and then rinsing in distilled H$_2$O, if necessary, depending on the level of contamination of the implant body.

Before the start of the plasma chemical coating process, the implant body is connected electrically to the anode of electrodes with protection against contact by means of a titanium or aluminum wire. The counterelectrode (cathode) is made of an acid-resistant stainless steel. The anode and cathode of the electrodes are connected to a voltage source capable of delivering a pulsed voltage. The current density is approx. 10 mA/cm$^2$.

After immersing the implant body in the aqueous solution, a constantly rising pulsed bath voltage is applied. On reaching the bath voltage range of more than 100 V, which is characteristic of the treatment of magnesium alloys in the electrolyte composition, plasma chemical surface effects occur. These create surface layers consisting of oxides, hydroxides and phosphates of the metallic base material of the implant body as well as additional compounds, which are recruited from elements of the electrolyte. In particular, due to the presence of the Sr$^{2-}$ ions, strontium carbonate is also formed, consisting of the carbon of ethylenediamine, the oxygen of the aqueous electrolyte and the strontium of strontium is hydroxide and/or strontium nitrate. Furthermore, strontium phosphate is also formed as a plasma chemical reaction product of potassium dihydrogen phosphate and water.

After reaching the coating voltage of approx. 250 V, the preset current density of approx. 10 mA/cm$^2$ drops to approx. 6 mA/cm$^2$. On reaching this level, the current supply is interrupted and the plasma chemical process is terminated. The layer thickness of the intermediate layer thereby formed preferably amounts to approx. 1 μm to approx. 20 μm, especially preferably between 1 μm and 8 μm, and depends to a significant extent on the bath voltage.

Then there is a multistep rinsing of the implant body in distilled water, separation of the implant from the contact wire and drying of the body of the implant in a circulating air oven at approx. 100° C.

After the plasma chemical coating process, which is concluded with the drying step described in the previous section, the implant body is suspended on a plastic string (e.g., polyamide) and then immersed in the solution to apply the magnesium stearate. The solution consists of 9 parts high-purity acetone or isopropanol and 1 part magnesium stearate, for example. The immersion process takes place at room temperature in a desiccator that can be evacuated. A vacuum of approx. 100 mbar is created in the desiccator by means of a pump. In this way the filigree surface structures and the microporous surface structures formed due to the previous plasma chemical pretreatment and/or the undercuts and complex structural shapes are effectively freed of any residual gas. Therefore, complete coverage of the stent surface by magnesium stearate may be accomplished in solution and the magnesium stearate also penetrates into the surface structures and undercuts. After a dwell time of approx. 3 minutes in the immersion bath, the desiccator is aerated, the implant is removed from the immersion bath and then dried at a temperature of 60° C. in a circulating air cabinet, still suspended from the plastic string. The layer thickness of the resulting magnesium stearate coating is in the range of approx. 0.5 µm to approx. 10 µm.

Due to the vacuum prevailing in the desiccator, the magnesium stearate is deposited very uniformly on the surface. A low drying temperature advantageously produces a slow release/evaporation of the solvent of the immersion solution, yielding a pore-free magnesium stearate layer. If the implant produced in this way is a stent, then the body provided with the first layer and the intermediate layer may be completed by adding a catheter and subjected to radiation sterilization.

In another exemplary embodiment, the plasma chemical treatment with the subsequent rinsing and drying prior to the immersion treatment to produce the magnesium stearate layer may also be omitted.

Implants produced by the method described here will degrade within the desired time frame. Surprisingly the degradation can also be controlled here by a layer (intermediate layer) which is designed to be porous.

What is claimed is:

1. A method for manufacturing a degradation-inhibiting first layer on a surface of an implant body, optionally an intraluminal endoprosthesis, whereby the body has at least one metallic material, which is biodegradable, comprising the following steps:
   a) preparing the body of the implant,
   b) applying a composition consisting essentially of magnesium stearate to at least a portion of the body surface to form the first layer, characterized in that the composition is applied by immersion in a solution consisting of magnesium stearate and a solvent, wherein the solvent is optionally acetone and/or isopropanol, and optionally at a temperature between approximately 10° C. and 40° C.

2. The method according to claim 1, characterized in that the composition is applied at a pressure which is lower than ambient pressure, optionally lower than approximately 90% of ambient pressure.

3. The method according to claim 1, characterized in that the body of the implant is dried at a temperature between approximately 30° C. and approximately 70° C., after applying the composition, whereupon the drying is optionally performed in a circulating air oven.

4. The method according to claim 1, characterized in that before applying the composition, at least a portion of the implant body surface is subjected to a plasma chemical treatment in an aqueous solution to create an intermediate layer in which an electric voltage generating the plasma is applied to the body of the implant.

5. The method according to claim 4, characterized in that a buffer, optionally potassium dihydrogen phosphate and/or sodium dihydrogen phosphate, is contained in the aqueous solution.

6. The method according to claim 4, characterized in that the body surface is treated electrochemically before plasma chemical treatment, optionally by electrochemical polishing.

7. The method according to claim 4, characterized in that plasma chemical treatment of the body surface is performed by applying a pulsed voltage to the body, the amplitude exceeding at least approximately 90 V over most of the treatment, optionally at least approximately 100 V and optionally rising in the course of the treatment.

8. The method according to claim 4, characterized in that the current density in plasma chemical treatment amounts to at least approximately 8 mA/cm$^2$, optionally at least approximately 10 mA/cm$^2$.

9. The method according to claim 4, characterized in that the aqueous solution contains one or more ions selected from the group consisting of phosphates, carbonates and silicates and/or $Sr^{2-}$ ions, whereby the $Sr^{2-}$ ions are optionally contained in the aqueous solution in a concentration of approximately 0.05 mol/L to approximately 2.0 mol/L $Sr^{2-}$.

10. The method according to claim 9, characterized in that the thickness of the intermediate layer is approximately 1 µm to approximately 20 µm.

11. The method according to claim 10, characterized in that the thickness of the intermediate layer is approximately 2 µm to approximately 8 µm.

12. The method according to claim 1, characterized in that a second layer comprising parylene is applied to the first layer.

13. The method according to claim 1, characterized in that the composition is applied to achieve a first layer thickness from approximately 0.5 µm to approximately 10 µm.

14. The method according to claim 13, characterized in that the first layer thickness is approximately 1.0 µm to approximately 5.0 µm.

15. The method according to claim 1, characterized in that the first layer is substantially pore free.

16. A method for manufacturing a degradation-inhibiting layer on a surface of an implant body, whereby the body has at least one metallic material, which is biodegradable, comprising the following steps:
   a) preparing the body of the implant,
   b) applying a solution consisting of magnesium stearate and a solvent to at least a portion of the body surface, and
   c) evaporating the solvent to form a layer of magnesium stearate on the body of the implant.

17. The method according to claim 16, wherein the body of the implant is roughened prior to the step of applying the solution.

18. The method according to claim 16, characterized in that before applying the solution, at least a portion of the body surface is subjected to a plasma chemical treatment in an aqueous solution to create an intermediate layer.

19. The method according to claim 16, wherein the solution is applied by spray coating.

20. The method according to claim 16, wherein the solvent is evaporated by drying the body surface at a temperature between approximately 30° C. and approximately 70° C., optionally in a circulating air oven.

* * * * *